United States Patent
Zwolinski et al.

(10) Patent No.: US 7,963,912 B2
(45) Date of Patent: Jun. 21, 2011

(54) ENDOSCOPIC TRANSLUMENAL SURGICAL METHODS USING A SHEATH

(75) Inventors: Andrew Zwolinski, Cincinnati, OH (US); Michael S. Cropper, Edgewood, KY (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1202 days.

(21) Appl. No.: 11/382,196

(22) Filed: May 8, 2006

(65) Prior Publication Data

US 2007/0260117 A1    Nov. 8, 2007

(51) Int. Cl.
*A61B 1/00* (2006.01)
(52) U.S. Cl. .................... 600/121; 600/114
(58) Field of Classification Search .......... 600/114, 600/115, 119–121, 207, 208, 104, 123–125, 600/127, 186; 604/171; 128/898
See application file for complete search history.

(56) References Cited

U.S. PATENT DOCUMENTS

| | | | |
|---|---|---|---|
| 3,908,663 A * | 9/1975 | Viek | 600/581 |
| 4,230,108 A | 10/1980 | Young | |
| 4,262,677 A * | 4/1981 | Bader | 600/572 |
| 4,535,773 A | 8/1985 | Yoon | |
| 4,581,028 A | 4/1986 | Fox, Jr. et al. | |
| 4,988,341 A | 1/1991 | Columbus et al. | |
| 5,104,389 A | 4/1992 | Deem et al. | |
| 5,236,423 A | 8/1993 | Mix et al. | |
| 5,256,149 A | 10/1993 | Banik et al. | |
| 5,257,617 A | 11/1993 | Takahashi | |
| 5,259,364 A * | 11/1993 | Bob et al. | 600/115 |
| 5,271,380 A | 12/1993 | Riek et al. | |
| 5,297,536 A | 3/1994 | Wilk | |
| 5,334,150 A | 8/1994 | Kaali | |
| 5,341,815 A | 8/1994 | Cofone et al. | |
| 5,391,156 A | 2/1995 | Hildwein et al. | |
| 5,458,131 A | 10/1995 | Wilk | |
| 5,518,501 A | 5/1996 | Oneda et al. | |
| 5,569,291 A | 10/1996 | Privitera et al. | |
| 5,569,292 A | 10/1996 | Scwemberger et al. | |
| 5,591,192 A | 1/1997 | Privitera et al. | |
| 5,599,305 A | 2/1997 | Hermann et al. | |
| 5,674,184 A | 10/1997 | Hassler, Jr. | |
| 5,685,820 A | 11/1997 | Riek et al. | |
| 5,743,880 A | 4/1998 | Hlavka | |
| 5,756,145 A | 5/1998 | Darouiche | |
| 5,817,061 A | 10/1998 | Goodwin et al. | |

(Continued)

FOREIGN PATENT DOCUMENTS

EA    1459688    9/2004

(Continued)

OTHER PUBLICATIONS

EP Search Report dated Jun. 12, 2008, App. No. 07251893.9, 10 pages.

*Primary Examiner* — John P Leubecker
*Assistant Examiner* — Victoria W Chen
(74) *Attorney, Agent, or Firm* — Nutter McClennen & Fish LLP

(57) ABSTRACT

The present invention provides methods and devices for shielding an endo scope during insertion through a body lumen, and in particular using a sheath for preventing contact between the endoscope (or trocar sleeve) and the body lumen, thus preventing bacteria from being carried into a body cavity.

5 Claims, 11 Drawing Sheets

U.S. PATENT DOCUMENTS

| | | |
|---|---|---|
| 5,871,440 A | 2/1999 | Okada |
| 6,030,365 A | 2/2000 | Laufer |
| 6,039,725 A | 3/2000 | Moenning et al. |
| 6,387,043 B1 | 5/2002 | Yoon |
| 6,432,044 B1 | 8/2002 | Lunsford et al. |
| 6,440,061 B1 | 8/2002 | Wenner et al. |
| 6,740,064 B1 | 5/2004 | Sorrentino et al. |
| 6,869,393 B2* | 3/2005 | Butler ............... 600/114 |
| 6,908,428 B2* | 6/2005 | Aizenfeld et al. ........... 600/123 |
| 6,918,871 B2 | 7/2005 | Schulze |
| 7,425,202 B2* | 9/2008 | Huang et al. ............... 600/564 |
| 2001/0044595 A1* | 11/2001 | Reydel et al. .............. 604/98.02 |
| 2002/0004646 A1 | 1/2002 | Manhes |
| 2002/0077646 A1 | 6/2002 | Truwit et al. |
| 2002/0133188 A1 | 9/2002 | O'Heeron et al. |
| 2002/0165521 A1 | 11/2002 | Cioanta et al. |
| 2003/0105386 A1* | 6/2003 | Voloshin et al. ............ 600/114 |
| 2004/0093000 A1 | 5/2004 | Kerr |
| 2004/0230165 A1 | 11/2004 | Prosl et al. |
| 2004/0254422 A1 | 12/2004 | Singh |
| 2004/0254545 A1* | 12/2004 | Rider et al. ............... 604/265 |
| 2004/0260245 A1 | 12/2004 | Clem et al. |
| 2005/0010237 A1 | 1/2005 | Niazi |
| 2005/0043682 A1* | 2/2005 | Kucklick et al. .......... 604/164.09 |
| 2005/0059934 A1 | 3/2005 | Wenchell et al. |
| 2005/0085773 A1 | 4/2005 | Forsberg |
| 2005/0107664 A1 | 5/2005 | Kalloo et al. |
| 2005/0107816 A1 | 5/2005 | Pingleton et al. |
| 2005/0203486 A1 | 9/2005 | Sommerich |
| 2006/0004254 A1* | 1/2006 | Voloshin et al. ............ 600/115 |
| 2006/0079925 A1 | 4/2006 | Kerr |
| 2006/0111612 A1 | 5/2006 | Matsumoto |
| 2006/0149305 A1 | 7/2006 | Cuevas et al. |
| 2006/0237022 A1* | 10/2006 | Chen et al. ................ 128/898 |
| 2006/0270900 A1 | 11/2006 | Chin et al. |
| 2007/0123840 A1* | 5/2007 | Cox ....................... 604/514 |

FOREIGN PATENT DOCUMENTS

| | | |
|---|---|---|
| EP | 1518499 A1 | 3/2005 |
| WO | 9915068 | 4/1999 |
| WO | 03082122 A1 | 10/2003 |
| WO | 2004064899 | 8/2004 |

* cited by examiner

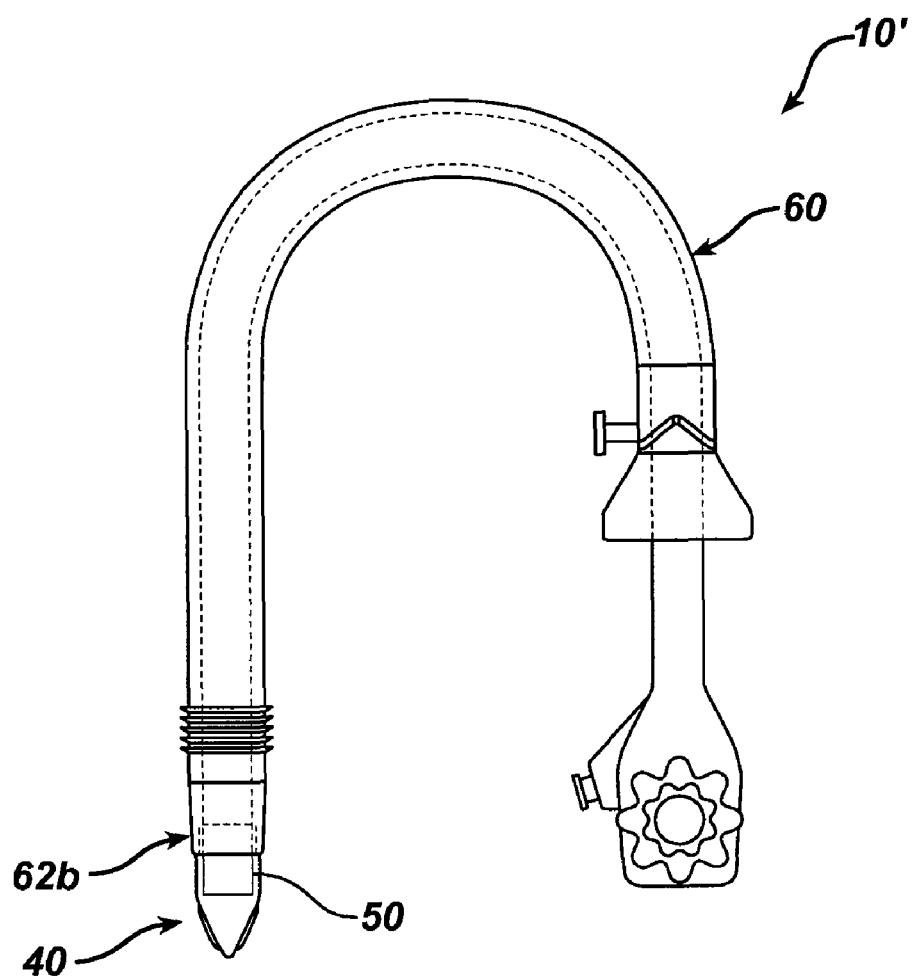

ENDOSCOPIC TRANSLUMENAL SURGICAL METHODS USING A SHEATH

FIELD OF THE INVENTION

The present invention relates to methods and devices for endoscopic translumenal surgery.

BACKGROUND OF THE INVENTION

Endoscopic surgery can be used to access the abdominal cavity via natural openings (mouth, anus, vagina, urethra) of the body and through the peritoneal lining of the abdominal cavity. Obviously, the size and shape of instruments that may be passed through a bodily lumen in order to perform a medical procedure in the abdominal cavity are greatly restricted due to the anatomical properties of the lumen. General surgeons, gastroenterologists, and other medical specialists, routinely use flexible endoscopes for intraluminal (within the lumen of the alimentary canal) examination and treatment of the upper gastrointestinal (GI) tract, via the mouth, and the lower GI tract, via the anus. In these procedures, the physician pushes the flexible endoscope into the lumen, periodically pausing to articulate the distal end of the endoscope using external control knobs, to redirect the distal tip of the endoscope. In this way, the physician may navigate the crooked passageway of the upper GI past the pharynx, through the esophagus and gastro esophageal junction, and into the stomach. The physician must take great care not to injure the delicate mucosal lining of the lumen, which generally may stretch open to a diameter in the range of about 15-25 mm, but normally has a non-circular cross sectional configuration when relaxed.

During such translumenal procedures, a puncture must be formed in the stomach wall or in the gastrointestinal tract to access the peritoneal cavity. One device often used to form such a puncture is a needle knife which is inserted through the working channel of the endoscope, and which utilizes energy to penetrate through the tissue. A guidewire is then fed through the endoscope and is passed through the puncture in the stomach wall and into the peritoneal cavity. The needle knife is removed, leaving the guidewire as a placeholder. A balloon catheter is then passed over the guidewire and through the working channel of the endoscope to position the balloon within the opening in the stomach wall. The balloon can then be inflated to increase the size of the opening, thereby enabling the endoscope to push against the rear of the balloon and to be fed through the opening and into the peritoneal cavity. Once the endoscope is positioned within the peritoneal cavity, numerous procedures can be performed through the working channel of the endoscope.

While current methods and devices used to penetrate tissue are effective, one drawback is that several exchanges and steps are required to form the opening. The small size of the opening formed can also create high resistance to advancing or retracting the endoscope, which is significantly larger than the opening. In the event the endoscope is retracted through the opening, it can also be difficult to locate the opening and re-insert the endoscope. Continued advancement and retraction of the endoscope can also be uncomfortable for the patient. Another drawback of current methods is that a non-sterile passageway is created from the stomach into the abdominal cavity, as the devices carry bacteria from the body lumen into the abdominal cavity.

Accordingly, there remains a need for improved endoscopic translumenal methods and devices.

SUMMARY OF THE INVENTION

The present invention provides various methods and devices for use in endoscopic surgery. In one embodiment, a translumenal trocar device is provided and includes an elongate flexible trocar sleeve having an inner lumen extending therethrough, and an elongate flexible obturator disposed through the trocar sleeve. The obturator has an inner lumen extending therethrough and sized to receive an endoscope therein, and a distal tip located at a distal end of the obturator and shaped to penetrate and guide the obturator and trocar sleeve through tissue to thereby insert an endoscope through tissue. At least one of the flexible trocar sleeve and the elongate flexible obturator can include at least two regions of differing rigidity to facilitate positioning translumenally.

The distal tip of the obturator can have a variety of configurations. In one embodiment, at least a portion of the distal tip is transparent. The distal tip can also have various shapes, for example it can have a generally conical shape. The distal tip can also include at least one cutting element for facilitating penetration thereof through tissue. The cutting element can be, for example, at least one blade formed on an outer surface of the distal tip and having a sharp, linear edge. In another embodiment, the distal tip can include at least one paddle extending outward from an outer surface of the distal tip and configured to be rotated to separate tissue. The tip can also include other features such as a bore formed therein for receiving a tissue cutting element therethrough.

The trocar sleeve can also have a variety of configurations. In one embodiment, the trocar sleeve can include at least one seal disposed therein which permits the passage of the obturator through the trocar sleeve while limiting or preventing the passage of fluid or gas therethrough. The seal can be disposed within a housing located at a proximal end of the trocar sleeve. The trocar sleeve can, in other embodiments, include a tapered distal portion that forms a smooth transition between the trocar sleeve and the distal tip of the obturator.

A translumenal introducer kit is also provided and includes an elongate flexible obturator disposable over an endoscope and having a distal tip located on a distal end thereof for seating the distal end of an endoscope to allow an image gathering unit on the endoscope to gather an image viewed through the distal tip. The distal tip can be shaped to penetrate through tissue. The kit can also include an elongate flexible trocar sleeve disposable over the obturator such that the obturator extends distally beyond a distal end of the trocar sleeve to guide the trocar sleeve through tissue being penetrated. In other embodiments, the kit can include an endoscope disposed through the elongate flexible obturator and having an optical image gathering unit at a distal end thereof.

A method for accessing a body cavity is also provided, and in one exemplary embodiment the method includes guiding an endoscope translumenally through a patient's body to position a distal end of the endoscope adjacent to tissue to be penetrated. A proximal end of the endoscope can remain outside of the patient's body. A distal tip located at the distal end of the endoscope is advanced through the tissue to guide the distal end of the endoscope through the tissue and into a body cavity. The endoscope and the distal tip can then be removed from a flexible trocar sleeve disposed around the endoscope such that the flexible trocar sleeve forms a working channel that extends from outside of the patient's body, translumenally, through the tissue, and into the body cavity. In one embodiment, the distal tip can be formed on a distal end of an obturator disposed around the endoscope and within the flexible trocar sleeve. After removing the endoscope, the endoscope can be removed from the obturator and inserted back into the flexible trocar sleeve. The method can also include, prior to advancing a distal tip through tissue, inserting a tissue cutting element through the endoscope and through a bore formed in the distal tip, and cutting the tissue with the cutting element. The endoscope and the distal tip can be guided translumenally through the tissue using an image of an area surrounding the distal end of the endoscope. The image can be gathered by an image gathering unit disposed within the distal end of the endoscope.

In another embodiment, an endoscope insertion assembly device is provided and includes an elongate flexible trocar sleeve having an inner lumen extending therethrough for longitudinally receiving an endoscope therein, and an end cap positionable within a distal end of the trocar sleeve and shaped to penetrate and guide the trocar sleeve through tissue. The end cap can removably disposable over a distal end of an endoscope, and in one embodiment at least a portion of the end cap is transparent to allow images to be viewed therethrough.

While the particular configuration of the end cap can vary, in one exemplary embodiment the end cap includes a portion adapted to be disposed over an endoscope, and a distal portion extending from the proximal portion and forming a viewing window to allow images to be viewed therethrough. The proximal portion can be formed from various materials, such as a resilient material to facilitate engagement with an endoscope. The distal portion can include a substantially planar region for facilitating viewing therethrough, or in other embodiments the distal portion can be in the shape of a parabola for facilitating viewing therethrough. The end cap can also include other features, such as a bore formed in the distal portion for receiving an endoscopic accessory, and/or one or more blades formed thereon for cutting tissue. The blade(s) can optionally be coupled to an energy source, such as an electrosurgical generator, an ultrasonic generator, a laser, or a heat source. In other embodiments, the end cap can includes at least one paddle extending outward from an outer surface of the end cap and configured to be rotated to separate tissue The trocar sleeve can also have a variety of configurations. In one embodiment, the trocar sleeve can include a tapered distal portion that tapers toward an outer surface of the end cap to form a substantially continuous outer surface with the end cap. The trocar sleeve can also optionally include at least one seal disposed therein which permits the passage of the end cap and an endoscope coupled to the end cap while limiting or preventing the passage of fluid or gas therethrough.

In other aspects, an endoscopic insertion device is provided and includes an end cap having a proximal housing configured to be removably disposed over a distal end of an endoscope, and a distal housing shaped to be inserted through tissue. At least a portion of the distal housing of the end cap can be transparent to allow an optical image gathering unit in an endoscope to view and gather and image therethrough. The proximal housing can have various configurations that allow it to mate to an endoscope. For example, the proximal housing can be formed from a resilient material to facilitate engagement with an endoscope. The distal housing can also have various configurations. In one embodiment, the distal housing can include a substantially planar region to facilitate viewing therethrough. In another embodiment, the distal housing can be in the shape of a parabola for facilitating viewing therethrough. The distal housing can also include other features, such as at least one blade formed thereon for cutting tissue, and/or a bore formed therethrough for receiving an endoscopic accessory.

In yet another embodiment, a translumenal introducer kit is provided and includes a plurality of end caps, each end cap including a proximal portion removably disposable over a distal end of an endoscope, and a distal portion configured to be inserted through tissue. The end caps can be the same, or they have different sizes and/or configurations.

In another embodiment, a method for accessing a body cavity is provided and includes guiding a distal portion of an endoscope to position an end cap disposed on a distal end of the endoscope adjacent to tissue to be penetrated, and advancing the end cap through the tissue to guide the distal end of the endoscope through the tissue and into a body cavity. An image of an area surrounding the distal end of the endoscope can be used to guide the endoscope translumenally and to advance the end cap through the tissue. The image can be gathered by an image gathering unit disposed within the distal end of the endoscope. In certain exemplary embodiments, the endoscope is guided over an endoscopic accessory pre-disposed through the tissue and the end cap is advanced over the endoscopic accessory and expands the tissue as it passes therethrough. The method can also include removing the endoscope and the end cap from a flexible trocar sleeve disposed around the endoscope such that the flexible trocar sleeve forms a working channel that extends from outside of the patient's body, translumenally, through the tissue, and into the body cavity. After removing the endoscope with the end cap from a flexible trocar sleeve, the end cap can be removed from the endoscope and the endoscope can be re-inserted into the flexible trocar sleeve. In yet another embodiment, prior to advancing the end cap through tissue, an endoscopic accessory can be inserted through the endoscope and through a bore formed in the end cap, and it can be used to cut the tissue.

In yet another embodiment, a method for introducing an endoscopic device is provided and includes positioning a proximal end of a flexible sheath in proximity to an opening of a body lumen, attaching a distal end of the flexible sheath to an endoscopic device, advancing a portion of the sheath through the body lumen while the proximal and distal ends of the sheath remain in proximity to the opening of the body lumen, and advancing the endoscopic device with the distal end of the sheath attached thereto through the body lumen. The flexible sheath forms a barrier between the endoscopic device and the body lumen.

In one embodiment, advancing a portion of the sheath can include advancing at least one support rod between the proximal and distal ends of the sheath to advance a portion of the sheath into the body lumen. The body lumen can be, for example, an esophagus and the proximal end of the sheath can be disposed in an oral cavity at the opening of the esophagus. The portion of the sheath that is advanced translumenally can thus be advanced into a patient's stomach. The sheath will thus prevent direct contact between the endoscopic device and the esophagus. The method can also include positioning a distal end of the endoscopic device within a patient's stomach, inserting an endoscopic accessory through the endoscopic device, and using the endoscopic accessory to form a puncture hole in the stomach to access the patient's abdominal cavity. The endoscopic accessory can be, for example, a flexible trocar sleeve having a transparent distal tip shaped to penetrate and guide the flexible trocar sleeve through tissue to thereby insert the endoscopic device through tissue.

In another exemplary method for introducing an endoscopic device, a mid-portion of a sheath can be advanced through a body lumen and into a stomach cavity. The sheath can have proximal and distal ends that remain external to the body lumen while the mid-portion of the sheath is being advanced. An endoscopic device, with the distal end of the sheath coupled thereto, can then be advanced through the sheath to position a distal end of the endoscopic device within the stomach cavity. The sheath will prevent contact between the body cavity and the endoscopic device. In certain exemplary embodiments, advancing a mid-portion of the sheath can include advancing at least one support rod between the proximal and distal ends of the sheath to advance the mid-portion of the sheath into the body lumen.

An endoscopic insertion system is also provided, and includes an endoscopic device configured to be introduced translumenally, and an elongate flexible sheath having proximal and distal ends with an inner lumen extending therethrough and configured to receive the endoscopic device. The proximal end of the flexible sheath can have a shape adapted to be disposed within a patient's mouth, and the distal end of the flexible sheath can be configured to mate to the endoscopic device. The system can also include at least one support rod adapted to advance a portion of the flexible sheath into a body lumen.

BRIEF DESCRIPTION OF THE DRAWINGS

The invention will be more fully understood from the following detailed description taken in conjunction with the accompanying drawings, in which:

FIG. 2A is a side, partially cross-sectional view of another embodiment of a trocar assembly having an end cap mated to a distal end of an endoscope that is inserted through a trocar sleeve;

DETAILED DESCRIPTION OF THE INVENTION

Figure 1A:
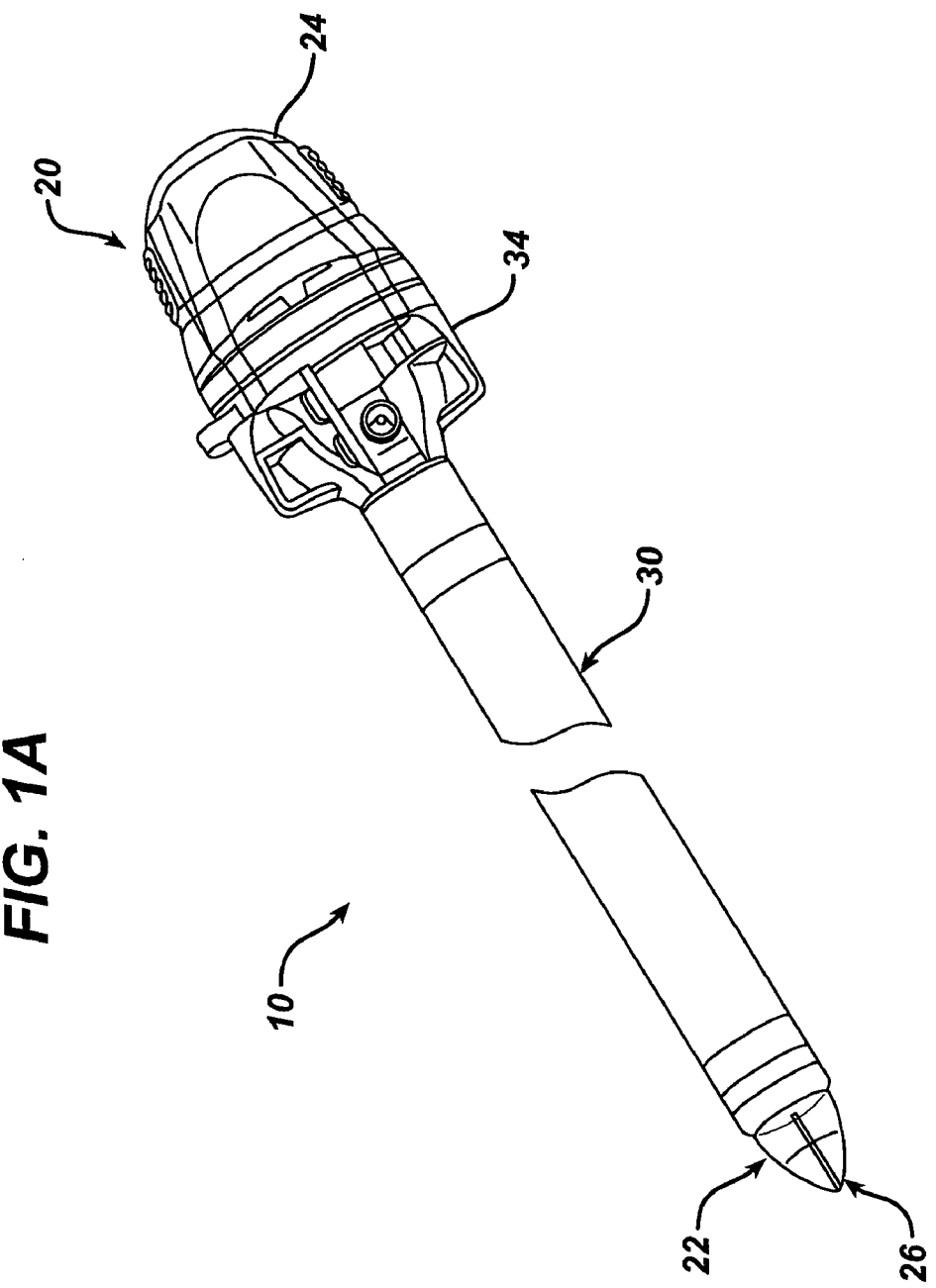
FIG. 1A is a perspective view of one embodiment of a trocar assembly having an obturator that houses an endoscope and a trocar sleeve disposed over the obturator.

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The present invention generally provides methods and devices for performing translumenal (e.g., transoral and transanal) procedures. In general, the methods and devices utilize a trocar assembly or trocar end cap that can facilitate insertion of an endoscope through tissue. In one embodiment, a flexible trocar assembly is provided for insertion through a body lumen. The trocar assembly can include an obturator having an inner lumen formed therethrough for receiving an endoscope therein, and a distal end that is adapted to facilitate insertion of the endoscope through tissue. The trocar assembly can also include a trocar sleeve that is disposable over the obturator. In use, once the trocar assembly is inserted through tissue, the trocar sleeve can function as a placeholder, allowing the endoscope and obturator to be removed. The endoscope can then be removed from within the obturator and reinserted through the trocar sleeve for use in performing various other procedures. In other embodiments, rather than using a trocar that houses the endoscope, an end cap can be removably disposed over a distal end of the endoscope. The endoscope and end cap can optionally be inserted through the elongate flexible trocar sleeve, and the assembly can be used to insert the endoscope through tissue. The sleeve can again function as a place holder after the assembly is inserted through tissue, thereby allowing the endoscope to be removed from the sleeve and the end cap to be removed from the endoscope. The endoscope can then be reinserted through the sleeve and thereby positioned through the puncture hole. The present invention also provides various techniques for inserting a flexible trocar assembly or end cap through tissue. In one embodiment, one or more blades can be formed on the obturator or end cap to allow the obturator or end cap to penetrate through the tissue. In another embodiment, the obturator or end cap can be configured to receive an endoscopic accessory, such as a needle knife, therethrough to allow the endoscopic accessory to penetrate through or cut the tissue. The obturator or end cap can then be guided over the endoscopic accessory and through the tissue, to thereby position the endoscope through the tissue. The present invention also provides methods and devices for shielding an endoscope during insertion through a body lumen, and in particular for preventing contact between the endoscope (or trocar sleeve) and the body lumen, thus preventing bacteria from being carried into a body cavity.

Figure 1B:
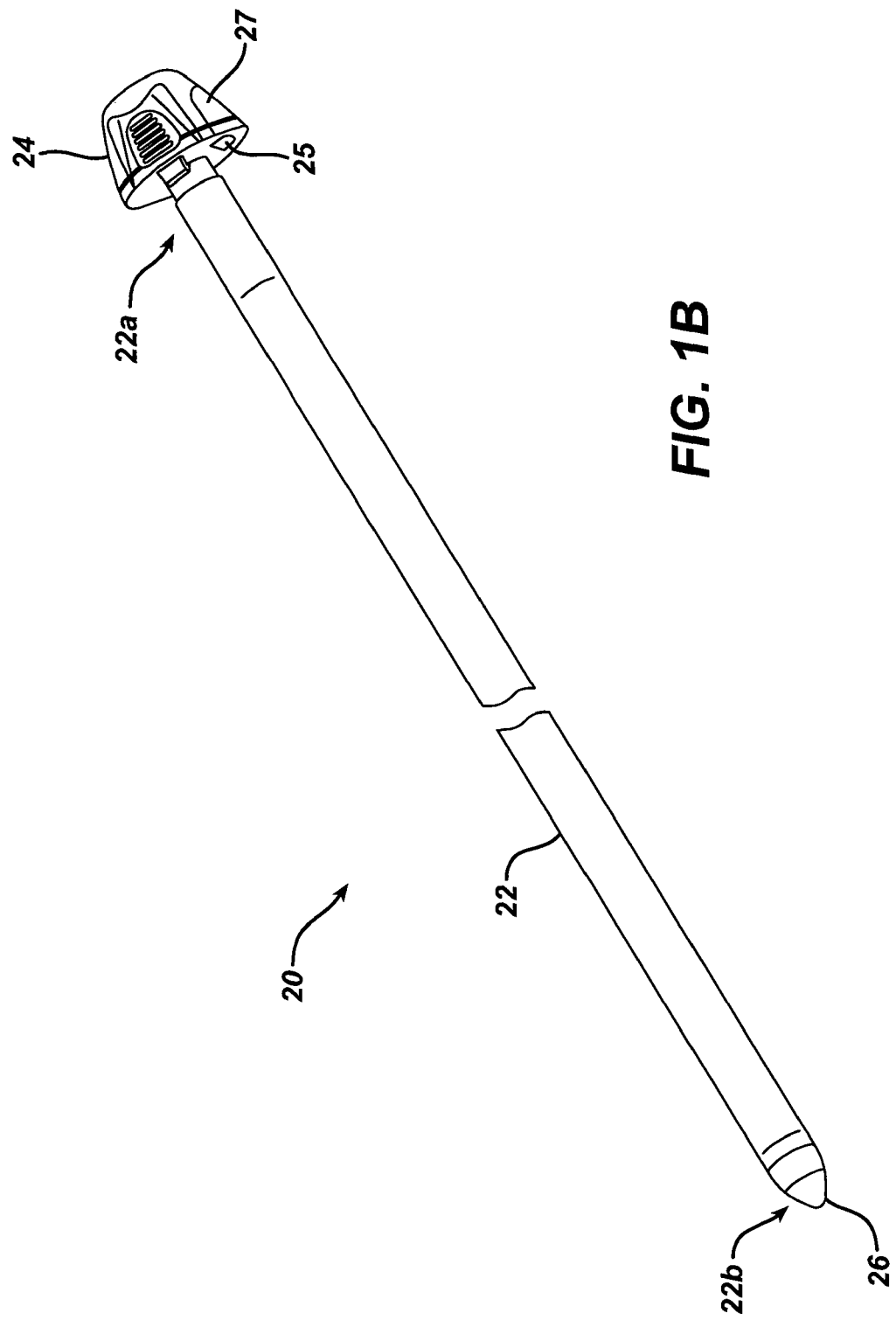
FIG. 1B is a perspective view of the obturator of FIG. 1A.
Figure 1C:
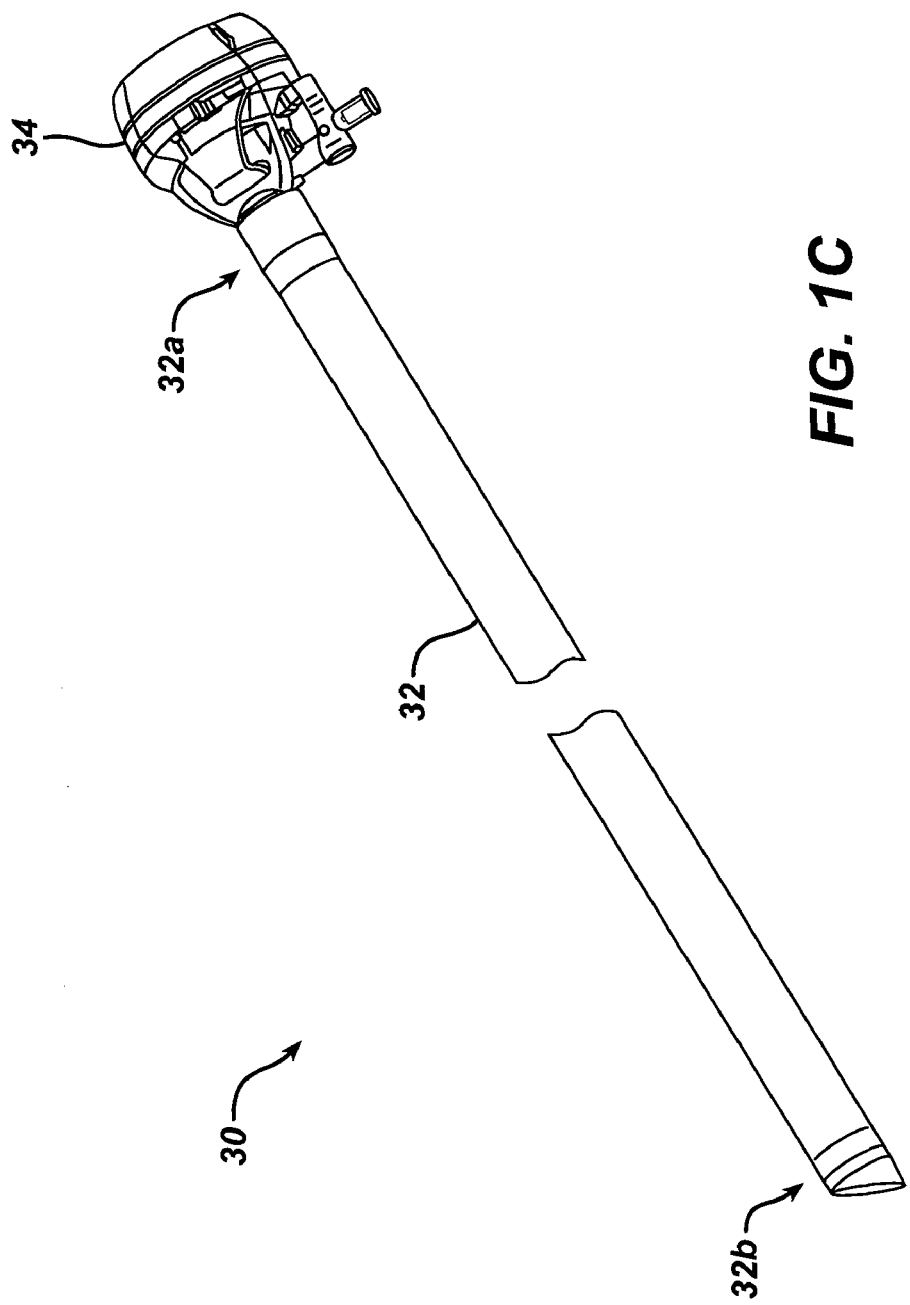
FIG. 1C is a perspective view of the trocar sleeve of FIG. 1A.

FIGS. 1A-1C illustrate one exemplary embodiment of a flexible trocar assembly 10 for use in advancing an endoscope translumenally and through tissue to introduce the endoscope into a body cavity, such as the abdominal cavity. As shown, the flexible trocar assembly 10 generally includes an obturator 20 having an inner lumen extending therethrough for receiving or housing an endoscope, and having a distal end 22b configured to facilitate insertion of the endoscope through tissue. The flexible trocar assembly 10 can also include an outer trocar sleeve 30 that is slidably disposed over the obturator 20, and that can function as a placeholder after the device 10 is inserted through tissue, as will be discussed in more detail below.

The obturator 20 is shown in more detail in FIG. 1B, and as shown the obturator 20 includes a hollow, elongate flexible shaft 22 having a proximal end 22a that is coupled to a housing 24 and a distal end 22b with a tip 26 that is adapted to be inserted through tissue. The size of the shaft 22 can vary, but it preferably has a length that allows it to be inserted translumenally, such as through a patient's esophagus, and it preferably has a diameter that allows an endoscope to be received therein. The shaft 22 can be made flexible using various techniques. For example, the shaft 22 can be formed from a flexible material, and/or it can include one or more features formed therein to facilitate flexible, such as a plurality of cut-outs or slots. In other embodiments, the shaft 22 can be formed from a plurality of linkages that are movably coupled to one another. The shaft 22 can also include regions that vary in flexibility. For example, certain portions of the shaft 22, such as the distal portion, can be more rigid than other portions of the shaft 22, such as the proximal portion, to correspond to the shape of a body lumen through which the shaft 22 is being inserted. This can be achieved by forming the shaft 22 from different materials, varying the diameter or thickness of the shaft 22, or using various other techniques know in the art. A person skilled in the art will appreciate that the shaft 22 can have virtually any configuration that allows the shaft 22 to flex as it is inserted through a tortuous body lumen. The shaft 22 can also include other features to facilitate use, such as one or more spiral wires embedded therein and configuration to preventing kinking of the shaft 22.

The housing 24 coupled to or formed on the proximal end 22a of the shaft 22 can have a variety of configurations, but in an exemplary embodiment the housing 24 is provided to allow the obturator 20 to removably mate to the trocar sleeve 30. For example, the housing 24 can include one or more mating elements to mate the housing 24 to a housing 34 formed on the trocar sleeve 30, as will be discussed in more detail below. While virtually any mating technique can be used, in the illustrated embodiment the housing 24 on the obturator 20 includes first and second tabs (only one tab 25 is shown) that extend distally from a distal surface of the housing 24. The tabs are configured to extend into corresponding bores formed in the housing 34 on the trocar sleeve 30. The tabs can also include protrusions formed adjacent to a terminal end thereof to allow the tabs to be engaged by an engagement mechanism formed within the bores, thereby fixedly mating the housing 24 on the obturator 20 to the housing 34 on the trocar sleeve 30. A release mechanism can be used to release the obturator 20 from the trocar sleeve 30. As shown in FIG. 1B, the first and second tabs are coupled to deflectable members (only one tab 25 and one deflectable member 27 is shown) that extend from opposed lateral sides of the housing 24. The deflectable members can be depressed to cause the tabs to move, thereby releasing the tabs from the engaging mechanism formed in the bores in the trocar sleeve 30. The housing 24 also preferably includes a lumen (not shown) formed therethrough for receiving an endoscope to allow the endoscope to be advanced into the obturator 20. A person skilled in the other will appreciate that various other techniques can be used to mate the housing 24 of the obturator 20 to the housing 34 of the trocar sleeve 30, including twist-lock mechanisms, threads, snap-fit, interference fit, etc. While not shown, an opening formed in the proximal-most end of the housing 24 can optionally include a seal disposed therein and effective to engage an outer surface of the endoscope to seal the endoscope with respect to the obturator 20. The seal is particularly useful during insufflation as it can prevent gases from escaping through the assembly. In particular, the seal can permit the passage of the obturator 20 and endoscope through the trocar sleeve 30 while limiting or preventing the passage of fluid or gas therethrough. A person skilled in the art will appreciate that the housing can include various other features known in the art, and that the housing can have virtually any shape and size. The obturator 20 also does not need to include a housing, but rather can merely be an elongate shaft that is slidably disposable over and endoscope and through a trocar sleeve.

The tip 26 on the distal end 22b of the elongate shaft 22 of the obturator 20 can also have a variety of configurations, and various exemplary configurations for the tip will be discussed in more detail below with respect to FIGS. 3A-5.

As indicated above, the flexible trocar assembly 10 can also include a trocar sleeve 30, which is shown in more detail in FIG. 1C. While the trocar sleeve 30 can have virtually any configuration, it preferably includes a hollow, elongate flexible shaft 32 that is configured to be slidably disposed over the obturator 20. The size of the flexible shaft 32 of the trocar sleeve 30 can vary, but it preferably has a length that is slightly less then a length of the shaft 22 of the obturator 20 such that the tip 26 of the obturator 20 extends distally beyond a distal end 32b of the elongate shaft 32. The diameter can also vary, but as indicated above, the diameter should be sufficient to allow the elongate shaft 32 of the trocar sleeve 30 to receive the elongate shaft 22 of the obturator 20 therein. The elongate shaft 32 of the trocar sleeve 30 can be made flexible using various techniques known in the art, including those previously discussed with respect to the elongate shaft 22 of the obturator 20. In an exemplary embodiment, the trocar sleeve 30 is a flexible sleeve having a coiled wire wrapped there around or embedded therein to prevent kinking, and having a slipping interior lining to facilitate smooth passage of the obturator 20 therethrough. The elongate shaft 32 of the trocar sleeve 30 can also include regions that vary in flexibility, as was also discussed above with respect to the elongate shaft 22 of the obturator 20.

The trocar sleeve 30 can also include other features to facilitate use of the trocar sleeve 30 with the obturator 20. For example, the distal end 32b of the trocar sleeve 30 can have an outer diameter that tapers distally, as shown, to form a substantially smooth continuous transition from the trocar sleeve 30 to the tip 26 of the obturator 20. The distal end 32b can also be angled as shown, or it can have various other configurations. In other exemplary embodiments, the distal end 32b can be transparent to facilitate viewing therethrough. The trocar sleeve 30 can also including a housing 34 formed on or coupled to a proximal end 32a of the elongate shaft 32. The housing 34 can be configured to removably mate to the housing 24 of the obturator 20, and in particular the housing 34 can include a proximal end with first and second bores (not shown) formed thereon and configured to receive the tabs formed on the distal end of the housing 24 on the obturator 20, as previously explained. The housing 34 can also include an inner lumen (not shown) formed therethrough and coaxial with the lumen in the elongate shaft 32 to allow the elongate shaft 22 of the obturator 20 to be inserted through the housing 34 and into the elongate shaft 32 of the trocar sleeve 30. While not shown, one or more seals can be disposed within the lumen in the housing 34 to engage an outer surface of the shaft 22 of the obturator 20 to seal the shaft 22 of the obturator 20 with respect to the trocar sleeve housing 34. Various seal or valve mechanisms are known in the art, including duck bill or double duck bill valves, zero-closure valves, gaskets, etc. A person skilled in the art will appreciate that the housing 34 can include various other features known in the art, and that the housing 34 can have virtually any shape and size. Alternatively, the trocar sleeve 30 does not need to include any housing and can merely be in the form of an elongate shaft which can optionally include a locking mechanism, such as a luer lock, for mating to and forming a seal about the obturator.

In other embodiments, at least a portion of the elongate shaft 32 of the trocar sleeve 30 can include a coating disposed thereon and configured to destroy any bacteria that comes into contact with the trocar sleeve 30 as the sleeve 30 is introduced translumenally. The coating can be, for example, an antimicrobial agent that is disposed along an external surface of the shaft 32 of the trocar sleeve 30. Other techniques can also optionally be used to help prevent the spread of bacteria as the device is inserted translumenally and into a body cavity.

In use, referring back to FIG. 1A, the obturator 20 can be inserted through and mated to the trocar sleeve 30 to form a flexible trocar assembly 10 that can be used to introduce an endoscope translumenally, and to position the endoscope through tissue and into a body lumen. In particular, an endoscope can be inserted into the opening in the proximal end of the housing 24 of the obturator 20 to position the distal end of the endoscope within or at least proximally adjacent to the tip 26 of the obturator 20. The obturator 20 can be inserted through the opening in the housing 34 of the trocar sleeve 30, and the housing 24 on the obturator 20 can be mated to the housing 34 on the trocar sleeve 30. As a result, the tip 26 of the obturator 20 will extend distally beyond the distal end 32b of the trocar sleeve 30. Once the endoscope is inserted through the trocar assembly 10, at least the distal end of the assembly 10 can be inserted translumenally, e.g., transorally or transanally, through a body lumen, and it can be inserted through tissue to gain access to a body cavity. Exemplary methods for inserting the assembly translumenally and through tissue will be discussed in more detail below.

Figure 2B:
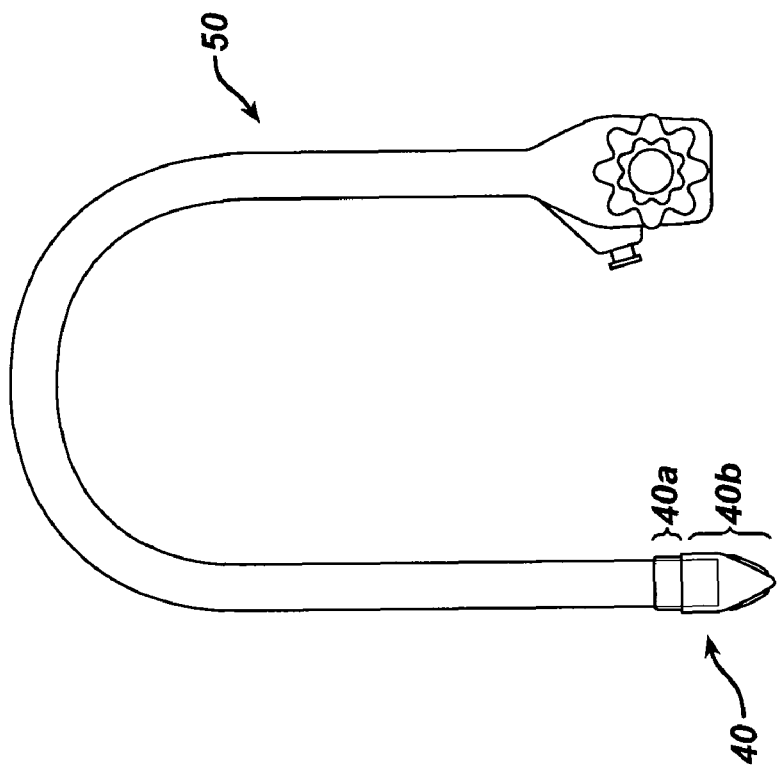
FIG. 2B is a side view of the trocar sleeve of FIG. 2A.
Figure 2C:
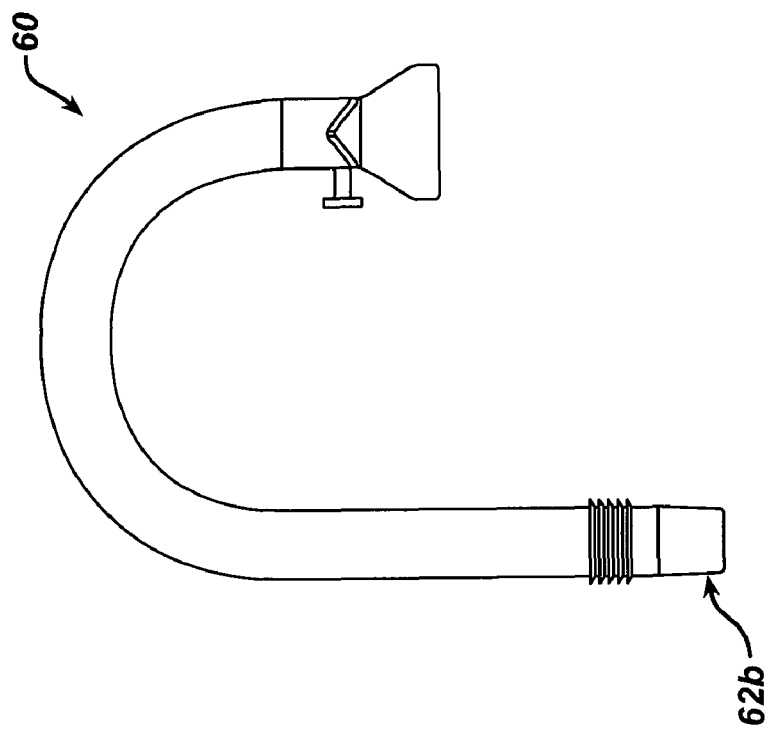
FIG. 2C is a side, partially cross-sectional view of the end cap and endoscope of FIG. 2A.

In another embodiment, rather than using an obturator 20 that houses the endoscope, an end cap, having a configuration similar to the tip 26 at the distal end 22b of the obturator 20, can be removably mated to the distal end of the endoscope. This is illustrated in FIGS. 2A and 2C, which show an end cap 40 removably mated to a distal end of an endoscope 50. The end cap 40 and endoscope 50 can optionally be inserted through a trocar sleeve 60, as shown in FIGS. 2A and 2B, to form a trocar assembly 10' that is similar to the trocar assembly 10 previously described with respect to FIGS. 1A-1C. While not described in detail, the trocar sleeve 60, shown separately in FIG. 2B, can have a configuration that is similar to the trocar sleeve 30 previously described with respect to the embodiment shown in FIGS. 1A-1C.

The end cap 40 can have a variety of configurations, and various techniques can be used to mate the end cap 40 to the distal end of an endoscope 50. In one exemplary embodiment, shown in detail in FIG. 2C, the end cap 40 can have a substantially cylindrical proximal portion 40a that can be slidably disposed over a substantially cylindrical distal end of the endoscope 50. The shape can, however, vary depending on the shape of the endoscope 50. The proximal portion 40a of the end cap 40 can also be configured to releasably engage the endoscope 50 to prevent the end cap 40 from disengaging with the endoscope 50 during use of the device. This can be achieved using, for example, a resilient material, an interference fit, a snap-fit, threads, or various other mating techniques known in the art. As further shown in FIG. 2C, the end cap 40 can also include a distal tip portion 40b that can be configured to facilitate insertion of the endoscope 50 through tissue. The particular configuration of the distal tip 40b can vary, and various exemplary distal tips will be discussed in more detail below with respect to FIGS. 3A-5.

In use, referring back to FIG. 2A, the end cap 40 can be mated to the distal end of the endoscope 50, and the endoscope 50 and end cap 40 can optionally be inserted through the trocar sleeve 60 to form a trocar assembly 10'. As previously explained with respect to the trocar sleeve 30 of FIG. 1C, the trocar sleeve 60 of FIG. 2A can include one or more seals disposed therein and effective to form a seal with the endoscope 50 inserted therethrough. As further shown in FIG. 2A, when the endoscope 50 is inserted through the trocar sleeve 60, the end cap 40, or at least the tip portion 40b of the end cap 40, will extend distally beyond a distal-most end 62b of the trocar sleeve 60 to allow the tip portion 40b of the end cap 40 to facilitate insertion of the assembly through tissue. The distal end 62b of the sleeve 60 can have various configurations, as previously explained, to allow the sleeve 60 and end cap 40 to fit together and have a substantially smooth continuous outer surface. Once the assembly is fully mated, at least the distal portion of the assembly can be inserted translumenally, e.g., transorally or transanally, through a body lumen, and it can be inserted through tissue to gain access to a body cavity. Exemplary methods for inserting the assembly translumenally and through tissue will be discussed in more detail below.

Figure 3A:
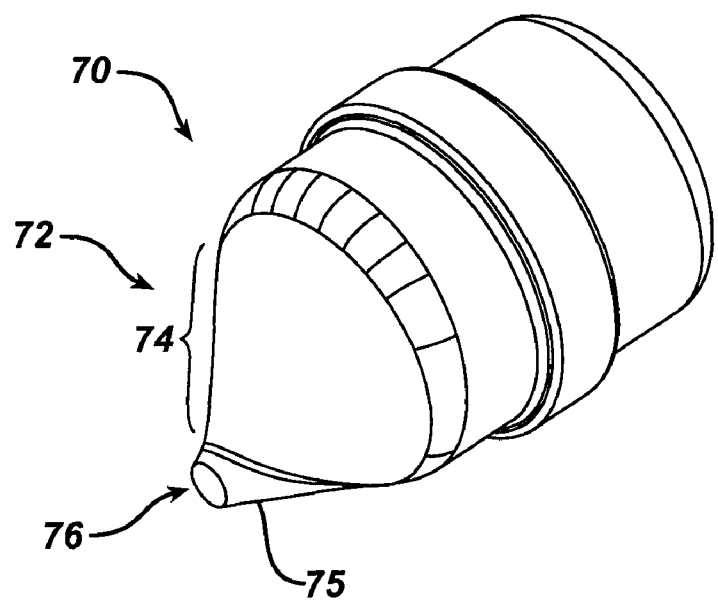
FIG. 3A is a perspective view of one exemplary embodiment of a tip configuration for use with the obturator of FIG. 1A or the end cap of FIG. 2A.
Figure 3B:
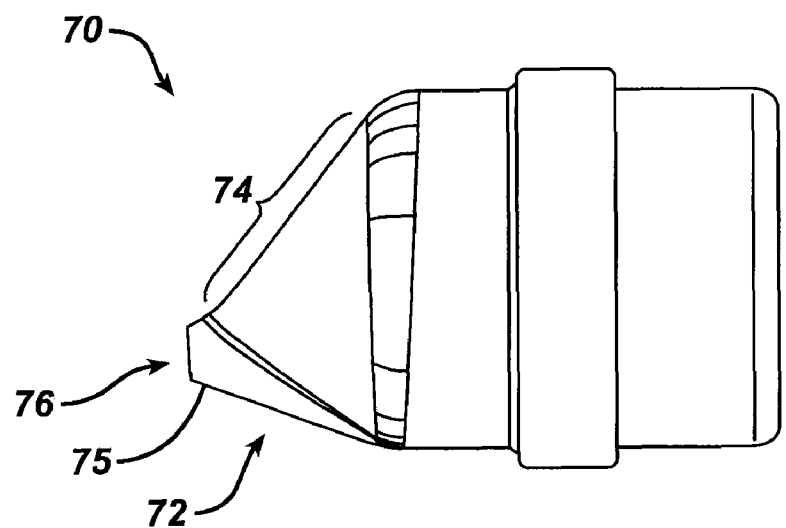
FIG. 3B is a side view of the tip of FIG. 3A.
Figure 4A:
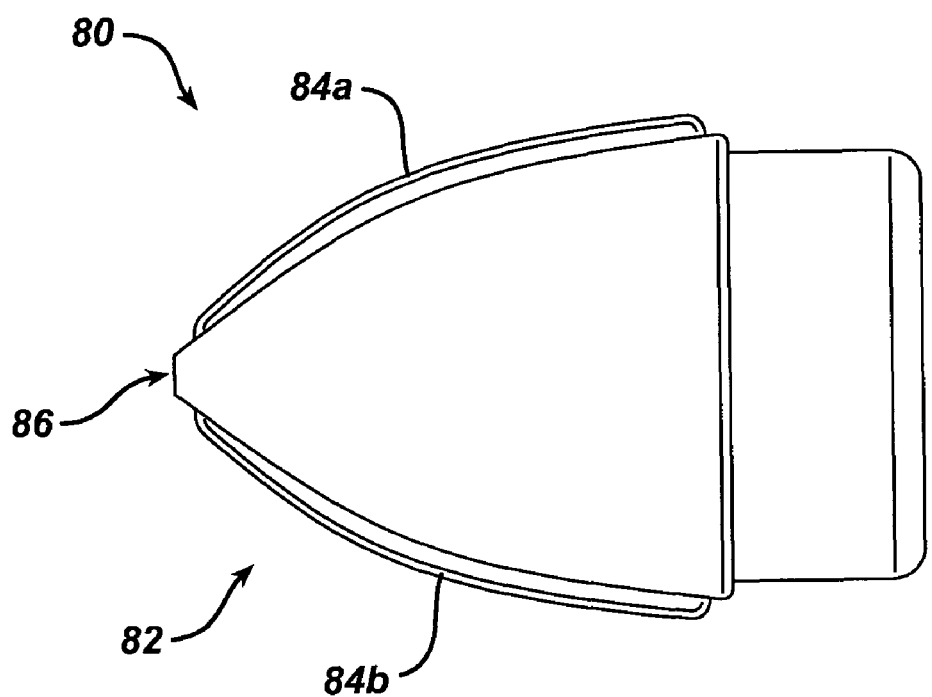
FIG. 4A is a side view of another exemplary embodiment of a tip configuration for use with the obturator of FIG. 1A or the end cap of FIG. 2A.
Figure 4C:
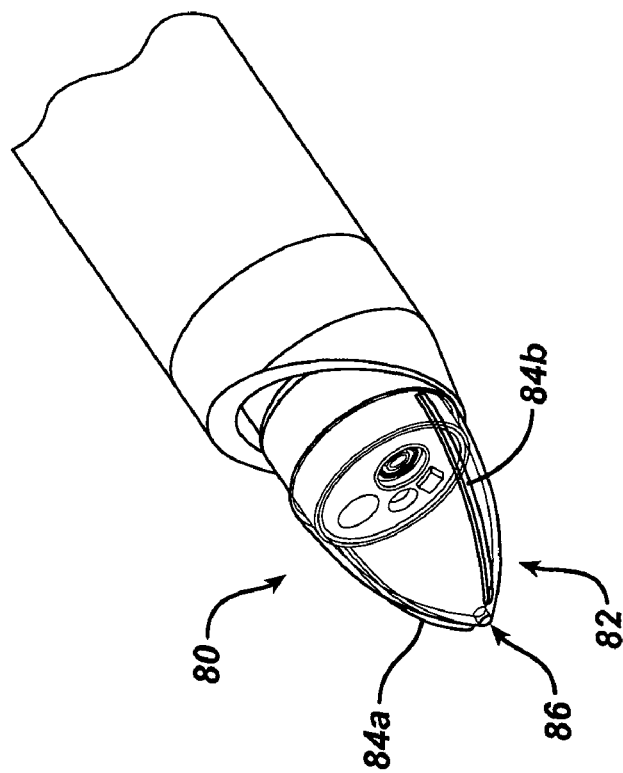
FIG. 4C is a perspective view of the tip and endoscope of FIG. 4B inserted through a trocar sleeve.
Figure 4B:
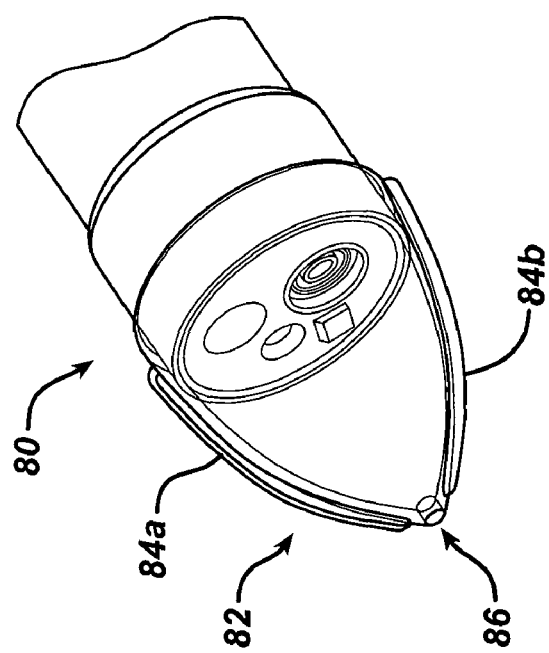
FIG. 4B is a perspective view of the tip of FIG. 4A mated to the distal end of an endoscope.

As previously indicated, the tip 26 at the distal end of the obturator 20 or the tip 40b at the distal end of the end cap 40 can have a variety of configurations depending on the intended use. In an exemplary embodiment, at least a portion and more preferably all of the tip is transparent or clear to allow an image gathering unit at the distal end of the endoscope to view and gather images through the tip. This will allow the endoscope to be used to guide the assembly through a body lumen and through tissue. The particular configuration of the transparent portion can vary in order to further facilitate viewing through the tip. For example, the materials and shape can be optimized to provide a smooth, clear viewing surface through which the endoscope can view and gather images. In one exemplary embodiment, the tip can be shaped so that a region of the tip is relatively flat. This is illustrated in the embodiment shown in FIGS. 3A-3B, which illustrate an end cap 70 having a tip 72 with a distal-most region 74 that has a minimal curvature such that the region 74 is somewhat flattened. In another exemplary embodiment, as shown in FIGS. 4A-4C, the tip 72 can taper distally and it can be in the shape of a parabola to prevent distortion of images gathered therethrough. The tip can also or alternatively be configured to enlarge an opening in tissue as the tip is advanced through the tissue. A person skilled in the art will appreciate that the tip can have a variety of configurations to facilitate viewing therethrough.

The particular configuration of the tip can also vary depending on the intended use of the tip. In one embodiment, the tip can have a configuration that allows the tip to cut and penetrate tissue through tissue. This can be achieved, for example, using one or more blades or cutting surfaces formed on the tip. FIGS. 4A and 4B illustrate one embodiment of an end cap 80 having a tip 82 with first and second cutting blades 84a, 84b formed on opposed sides thereof and extending between proximal and distal ends of the tip 82. The cutting blades 84a, 84b protrude above the outer surface of the tip 82, and have sharp edges to cut through tissue. The cutting blades 84a, 84b can also be configured to couple to an energy source to facilitate cutting of tissue. For example, a cautery wire can be coupled to the blades and it can extend through the endoscope attached to the end cap 80 to allow a proximal end of the wire to connect to an energy source. In another embodiment, the blades can be in the form of paddles that do not cut tissue, but rather merely extend outward from an outer surface of the tip. The paddles can have a generally planer, elongate configuration, and in use they can be configured to separate a cut or slit formed in tissue. For example, the paddles can be rotated to spread open an elongate cut made through tissue. The cutting blades can also be used to spread apart tissue, and/or to facilitate enlargement of a puncture hole formed through tissue. A person skilled in the art will appreciate that the cutting blades can be formed integrally with the tip, such that the tip and blades are formed as a single piece of material, or they can be separate from and mated to the tip. As previously mentioned, the tip can also taper distally to facilitate insertion and penetration through tissue. As further shown in FIGS. 4A-4C, the tip 82 can also include other features such as a bore 86 formed in the distal-most end thereof and configured to receive an endoscopic accessory therethrough, such as a guide wire, or a cutting element such as a needle knife or sphinctertome. The assembly can be inserted translumenally along the endoscopic accessory, or the endoscopic accessory can be introduced into the device at various stages of a procedure.

In another embodiment, rather than being configured to penetrate through tissue, the tip can be configured to facilitate insertion through the tissue and a separate endoscopic accessory can be used in coordination with the tip. For example, as previously described, FIGS. 3A-3B illustrate a tip 72 having a region 74 that is substantially planar. As further shown, the tip 72 can also include a protruding portion with a bore 76 formed therein for receiving an endoscopic accessory, such as a guide wire or a cutting tool, such as a needle knife or sphinctertome. The protruding portion 75 can be centrally located, but in an exemplary embodiment it is offset from a central axis of the endoscope so as to allow the protruding portion 75 to be positioned in axial alignment with a working channel of the endoscope, and to the allow the planar region 74 to be positioned in axial alignment with the viewing element in the endoscope. The protruding portion 75 can also taper distally toward the bore 76 to facilitate insertion of the tip through tissue.

Figure 5:
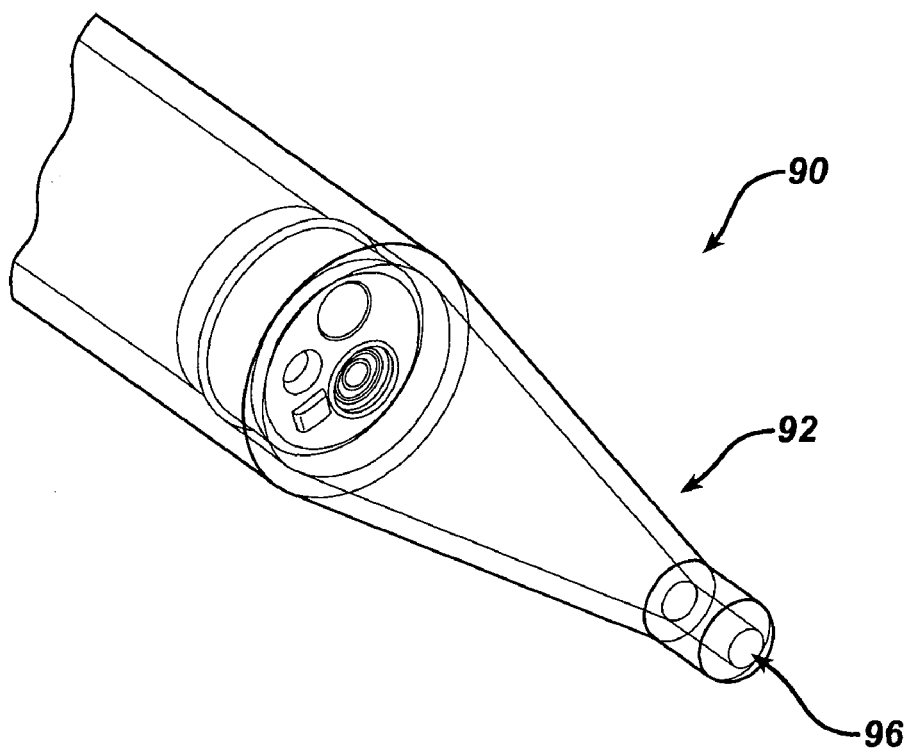
FIG. 5 is a perspective view of another embodiment of a tip configuration for use with the obturator of FIG. 1A or the end cap of FIG. 2A, showing the tip formed on the distal end of an obturator.

FIG. 5 illustrates another embodiment of a tip 92, shown formed on the distal end of an obturator 90, that is preferably configured to be used in combination with an endoscopic accessory, such as a guide wire or a cutting tool, such as a needle knife or sphinctertome. In this embodiment, the tip 92 has a generally conical configuration and tapers distally toward an opening or bore 96 formed in the distal-most end thereof. The bore 96 is co-axial with an axis of the endoscope, however since the tip 92 has an elongated length, any endoscopic accessory inserted through a working channel of the endoscope can move inward to be inserted through the bore 96.

A person skilled in the art will appreciate that the tip of the obturator or the end cap can have a variety of other configurations, and the tips shown in the figures are merely exemplary embodiments of tip configurations. By way of non-limiting configuration, various other exemplary tip configurations are disclosed in U.S. Pat. No. 5,591,192 of Privitera et al. entitled "Surgical Penetration Instrument Including an Imagining Element, and U.S. Pat. No. 5,569,292 of Scwemberger et al. entitled "Surgical Penetration Instrument With Transparent Blades and Tip Cover," which are hereby incorporated by reference in their entireties. The tip can also include other features. By way of non-limiting example, the tip can be configured to be energized to facilitate insertion and/or penetration of the tip through tissue.

Figure 6A:
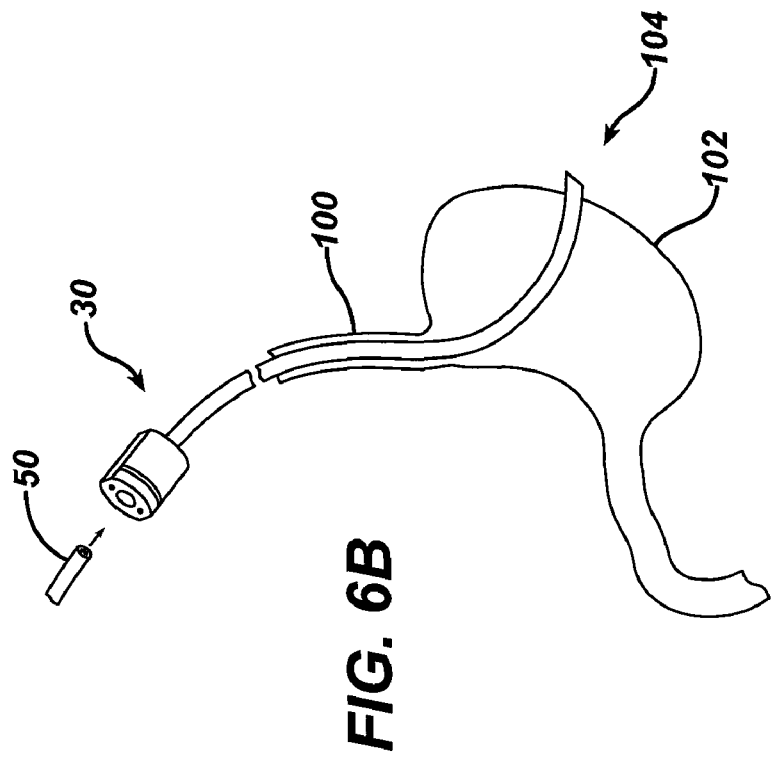
FIG. 6A is an illustration showing the trocar assembly of FIG. 1A inserted translumenally through an esophagus with the distal end penetrated through the stomach wall.
Figure 6B:
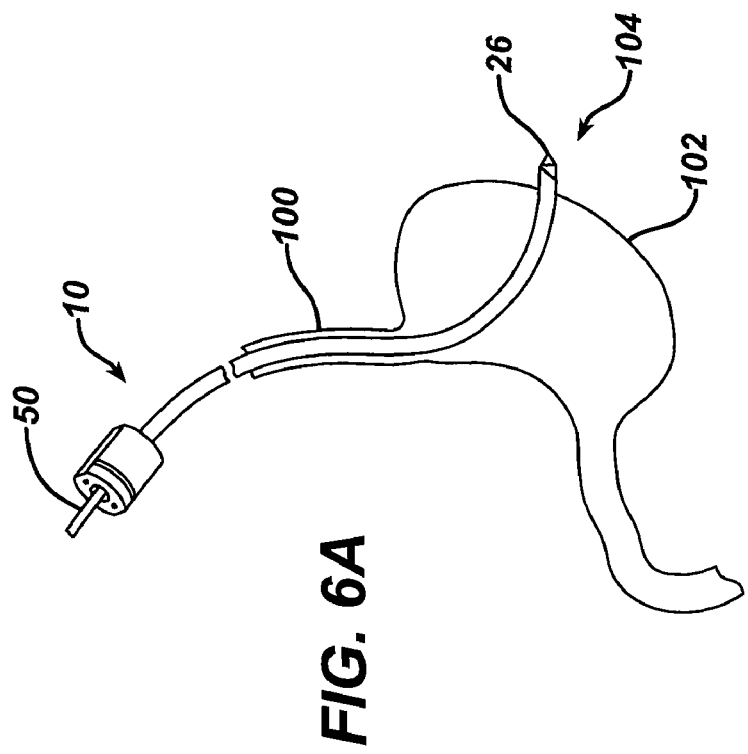
FIG. 6B is an illustration showing the trocar assembly of FIG. 6A, with the obturator and endoscope removing from the trocar sleeve, and the endoscope about to be re-inserted through the trocar sleeve.

FIGS. 6A and 6B illustrate one exemplary method for introducing an endoscope translumenally. The method is shown in conjunction with the device of FIGS. 1A-1C, however a person having ordinary skill in the art will appreciate that the device of FIGS. 2A-2C can be used, and that the device can have various other configurations, as previously described herein and as known in the art. In general, assembled device 10 is inserted translumenally, e.g., transorally or transanally, to position the distal end of the assembly at a desired location at which tissue is to be penetrated. FIGS. 6A-6B illustrate the assembly inserted transorally through a patient's esophagus 100 to position the distal end of the device within the stomach 102, and to subsequently penetrate through the stomach wall to position the distal end within the abdominal cavity 104. The device 10 can optionally be guided through the body lumen using a steering mechanism on the endoscope 50, using a steering mechanism that is coupled to the trocar assembly, or using other techniques known in the art.

Once the distal end of the trocar assembly 10 and endoscope 50 are positioned at the desired tissue penetration site, e.g., in the stomach 102, the tip 26 can be inserted through tissue. As previously explained, various techniques can be used to penetrate through the tissue. In the embodiment shown in FIGS. 1A-1C and FIGS. 6A-6B, the tip 26 of the obturator 20 includes cutting blades formed thereon that can cut through tissue, allowing the trocar assembly 10 to be directly penetrated through the tissue. The cutting blades can optionally be connected to an energy source to cauterize the tissue as the tip 26 is inserted therethrough. Where the tip 26 does not include cutting blades, such as the tip 72 shown in FIGS. 3A-3B, or in addition to the cutting blades, a cutting tool, such as a needle knife or sphinctertome, can be inserted through the working channel of the endoscope 50 and through the bore 76 in the tip 72. The needle knife or sphinctertome can then be energized to penetrate or cut through the tissue. The assembly can be guided over the needle knife or sphinctertome to guide the tip 72 through the puncture formed in the tissue by the needle knife, or alternatively the cutting device can be replaced by a guide wire and the assembly can be guided over the guide wire through the puncture. A person skilled in the art will appreciate that various other techniques can be used to penetrate through the tissue.

Once the distal end of the assembly 10 is inserted through the tissue, as shown in FIG. 6A, the obturator 20 and endoscope 50 (or, for the embodiment of FIGS. 2A-2C, the end cap 40 and endoscope 50) can be removed from the trocar sleeve 30. The trocar sleeve 30 will function as a placeholder for the puncture formed in the tissue, as the trocar sleeve 30 will remain extending through the puncture and into the body cavity, e.g., the abdominal cavity, as shown in FIG. 6B. The endoscope 50 can then be removed from the obturator 20 (or, for the embodiment of FIGS. 2A-2C, the end cap 40 can be removed from the endoscope 50), and the endoscope 50 can be reinserted through the trocar sleeve 30. FIG. 6B illustrates the endoscope 50 about to be introduced into the trocar sleeve 30. Once the endoscope 50 is advanced through the trocar sleeve 30 to position the distal end of the endoscope 50 within the body cavity, e.g., the abdominal cavity 104, various medical procedures can be performed. The trocar sleeve 30 can remain in place or it can be removed leaving the endoscope 50 in place.

While not shown, the assembly can also be used in conjunction with an expandable member used to expand the size of the puncture hole to facilitate insertion of the assembly therethrough. For example, a cutting device can be used to form a puncture in the tissue, and an expandable member, such as a balloon, disposed on the cutting device or on a separate device can be advanced and positioned within the puncture. The expandable member can then be expanded to increase the size of the puncture. The endoscope can then be advanced, pushing the expanded expandable member and the endoscope through the puncture. Where this technique is used, it may not be necessary to use an obturator or end cap with the endoscope. Rather, the trocar sleeve can be positioned over the endoscope and passed through the puncture with the endoscope. The endoscope and expandable member can then be removed, leaving the trocar sleeve in place for receiving other devices therethrough.

Figure 7A:
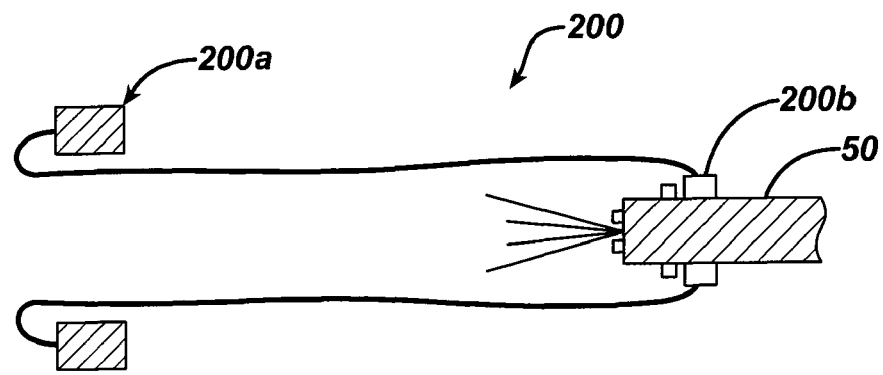
FIG. 7A is a side view of one embodiment of a protective barrier for shielding an endoscopic or laparoscopic device during insertion, showing a distal end of the barrier coupled to an endoscope.
Figure 7B:
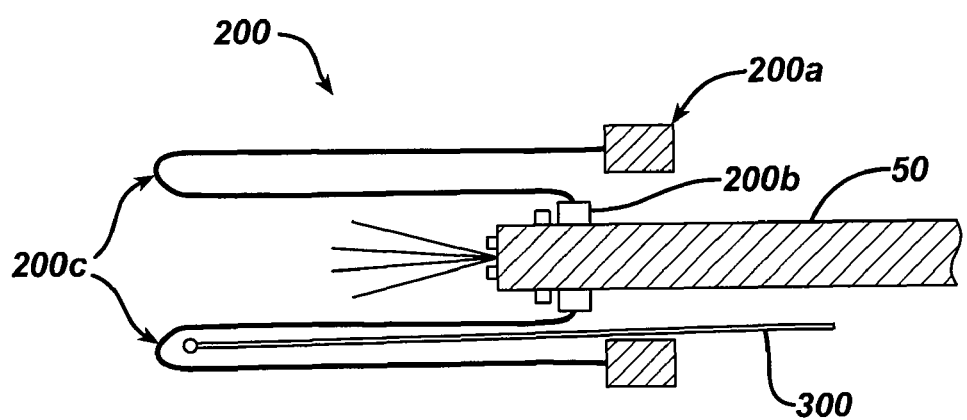
FIG. 7B is a side view of the protective barrier and endoscope of FIG. 7A showing the distal end and an endoscope inserted through the proximal end of the protective barrier.

In another embodiment of the present invention, a protective barrier is provided to facilitate insertion of an endoscopic device, such as an endoscope, overtube, trocar assembly, or any other endoscopic device, through a body lumen. FIGS. 7A-7B illustrate one exemplary embodiment of a protective barrier 200 and method for using the same. The particular configuration of the barrier 200 can vary, but in an exemplary embodiment the barrier 200 has a generally elongate hollow configuration with proximal and distal ends 200a, 200b. One of the ends, e.g., the distal end 200b, can be adapted to mate or attach to a distal end of an endoscopic device, such as endoscope 50, and the other end, e.g., the proximal end 200a, can be configured to remain external to the patient or to be disposed and retained within an opening to a body lumen, such as the patient's oral cavity. The particular configuration of each end can vary. For example, the distal end 200b can be formed from a resilient material to allow the distal end 200b to be disposed over and engage an endoscope 50 or other device. The proximal end 200a can be shaped to fit within an opening of a body cavity, such as an oral cavity, or it can merely be a terminal end of the tube. In an exemplary embodiment, the proximal end 200a is flared outward to facilitate introduction of the endoscope 50 or other device and distal end 200b of the barrier 200 therethrough. In other embodiments, where the barrier 200 is formed from a resilient material, the ends 200a, 200b can merely be rolled over or folded onto themselves to form a soft terminal end surface.

At least a portion of the barrier 200 can also be formed from a flexible or resilient material to facilitate insertion of at least the flexible or resilient portion through tissue. In the embodiment shown in FIGS. 7A-7B, the entire barrier 200 is flexible to allow the mid-portion of the barrier 200 to be inserted translumenally, as will be discussed in more detail below. In other embodiments, the barrier can include a flexible or resilient portion and a portion that is more rigid. For example, the barrier can be formed using a standard overtube and a flexible sheath that is coupled to the overtube. In use, as will be discussed below, the overtube can form an inner sleeve of the device, and the flexible sheath can form an outer sleeve. The use of an overtube can provide support to the esophagus, which may be important in certain applications, such as an obese patient, prior conditions and operations, etc.

In use, as shown in FIGS. 7A-7B, a mid-portion 200c of the barrier 200 is inserted translumenally preferably through the entire length of the body lumen, such as an esophagus, while the proximal and distal ends 200a, 200b remain outside of or just within the opening to the body cavity. Various inserter tools known in the art can be used to insert the mid-portion translumenally. For example, at least one support rod 300 can be positioned between the proximal end distal ends 200a, 200b of the barrier 200 and it can be advanced into the mid-portion 200c of the barrier 200 and through a body lumen to insert the mid-portion 200c through the body lumen. As a result, the barrier 200 will include an inner sheath and an outer sheath that extend through the lumen. Where the barrier includes an overtube or other more rigid portion, the flexible portion can form the outer sleeve, and the overtube can form the inner sleeve. Alternatively, the flexible portion can have a length that allows the flexible portion to form both the inner and outer sleeves, and the overtube can remain outside the body.

The distal end 200b of the barrier 200 can be coupled to an endoscopic device, such as endoscope 50, and once the mid-portion 200c is inserted through the body lumen, the endoscope 50, with the distal end 200b of the barrier 200 attached thereto, can be inserted into the proximal end 200a of the barrier 200 and through the body lumen. Again, where the barrier includes an overtube, the overtube can couple to the endoscope or other device and the overtube and endoscope can be inserted together through the flexible portion. As the endoscope 50 is being inserted through the barrier 200, the barrier 200 will prevent contact between the endoscope 50 and the body lumen, thereby shielding the endoscope 50 and preventing any bacteria within the body lumen from being brought into a body cavity, such as the stomach. In an exemplary embodiment, the barrier 200 preferably has a length that allows the barrier 200 to extend through the entire body lumen, such as the esophagus, and into, for example, the stomach so there is no contact between the endoscope and the esophagus. Once the endoscope 50 is positioned in the stomach or other body lumen, various other procedures, such as those previously described, can be performed. For example, an endoscopic accessory can be inserted through the endoscopic device to facilitate insertion of the endoscopic device through tissue. A person skilled in the art will appreciate that the barrier can be used in a variety of endoscopic and laparoscopic procedures, and it can have a variety of configurations to facilitate mating to and use with an endoscopic or laparoscopic device.

In another exemplary embodiment, the various devices disclosed herein, or portions thereof, can be designed to be disposed of after a single use, or they can be designed to be used multiple times. For example, after at least one use, the device can be disassembled, followed by cleaning or replacement of particular pieces, and subsequent reassembly. By way of example, the end cap disclosed herein can be provided as a kit containing multiple end caps (the sizes can be the same or they can vary). After at least one use of the device, the end cap can be removed, the endoscope can be cleaned, and a new end cap can be placed on the endoscope to prepare for subsequent use. The various other devices disclosed herein can also be disassembled after at least one use, and any number of the particular pieces can be selectively replaced or removed in any combination. Replacement of pieces can also include replacement of portions of particular elements. Upon cleaning and/or replacement of particular parts, the device can be reassembled for subsequent use either at a reconditioning facility, or by a surgical team immediately prior to a surgical procedure. Those skilled in the art will appreciate that reconditioning can utilize a variety of techniques for disassembly, cleaning/replacement, and reassembly. Use of such techniques, and the resulting reconditioned device, are all within the scope of the present application.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A method for introducing an endoscopic device, comprising:
    advancing a mid-portion of a sheath through a body lumen and into a stomach cavity, the sheath having proximal and distal ends that remain external to the body lumen while the mid-portion of the sheath is being advanced; and
    with the mid-portion of the sheath advanced through the body lumen and into the stomach cavity, advancing an endoscopic device from external to the stomach cavity, with the distal end of the sheath coupled thereto, through the sheath to position a distal end of the endoscopic device within the stomach cavity, the sheath preventing contact between the stomach cavity and the endoscopic device.

2. The method of claim 1, wherein advancing a mid-portion of the sheath comprises advancing at least one support rod between the proximal and distal ends of the sheath to advance the mid-portion of the sheath into the body lumen.

3. The method of claim 1, wherein the body lumen comprises an esophagus and the proximal end of the sheath is disposed in an oral cavity at the opening of the esophagus.

4. The method of claim 1, further comprising inserting an endoscopic accessory through the endoscopic device, and forming a puncture hole in the stomach to access the patient's abdominal cavity.

5. The method of claim 4, wherein the endoscopic accessory comprises a flexible trocar sleeve having a transparent distal tip shaped to penetrate and guide the flexible trocar sleeve through tissue to thereby insert the endoscopic device through tissue.

* * * * *